(12) United States Patent
Wienecke et al.

(10) Patent No.: US 7,084,965 B2
(45) Date of Patent: Aug. 1, 2006

(54) ARRANGEMENT AND METHOD FOR INSPECTING UNPATTERNED WAFERS

(75) Inventors: Joachim Wienecke, Jena (DE); Kuno Backhaus, Zoellnitz (DE)

(73) Assignee: Vistec Semiconductor Systems Jena GmbH, Jena (DE)

( * ) Notice: Subject to any disclaimer, the term of this patent is extended or adjusted under 35 U.S.C. 154(b) by 415 days.

(21) Appl. No.: 10/224,415

(22) Filed: Aug. 21, 2002

(65) Prior Publication Data

US 2003/0038932 A1    Feb. 27, 2003

(30) Foreign Application Priority Data

Aug. 22, 2001   (DE) ................................ 101 41 051

(51) Int. Cl.
  G01N 21/00   (2006.01)
  G01N 21/86   (2006.01)
  G01N 21/88   (2006.01)
  G01R 31/26   (2006.01)

(52) U.S. Cl. ............................. 356/237.2; 250/559.39; 250/559.45; 438/16

(58) Field of Classification Search .. 356/237.1–237.5, 356/241.1–241.6, 238.1–238.3, 445–448; 250/559.4–559.45; 382/141, 145, 147, 144, 382/148, 149; 348/125, 126, 128; 438/7, 438/16

See application file for complete search history.

(56) References Cited

U.S. PATENT DOCUMENTS

| | | | | |
|---|---|---|---|---|
| 4,512,659 A | * | 4/1985 | Galbraith et al. | 356/243.1 |
| 5,256,204 A | * | 10/1993 | Wu | 118/719 |
| 5,383,018 A | * | 1/1995 | Sadjadi | 356/243.4 |
| 5,719,495 A | * | 2/1998 | Moslehi | 324/158.1 |
| 6,016,562 A | * | 1/2000 | Miyazaki et al. | 714/724 |
| 6,407,373 B1 | * | 6/2002 | Dotan | 250/201.3 |
| 6,411,377 B1 | * | 6/2002 | Noguchi et al. | 356/237.4 |
| 6,747,734 B1 | * | 6/2004 | Ritzdorf et al. | 356/237.5 |
| 2002/0176074 A1 | * | 11/2002 | Hasan | 356/237.5 |

OTHER PUBLICATIONS

F. Passek et al., "Discrimination of Defects on Epitaxial Silicon Wafers", Electrochemical Society Proceedings, vol. 97/22, pp. 438ff, 1997.

* cited by examiner

Primary Examiner—Gregory J. Toatley, Jr.
Assistant Examiner—Gordon J. Stock, Jr.
(74) Attorney, Agent, or Firm—Foley & Lardner LLP

(57) ABSTRACT

The invention concerns an arrangement (1) for inspecting preferably unpatterned wafers, and comprises: a first optical inspection device (2) for examining reference wafers (R), which operates using image data processing methods and thereby recognizes defects on the reference wafers; a scattered-light measuring instrument (3) that is calibrated with the reference wafers (R) by defining at least one threshold value for the recognition of defects on wafers (W) to be inspected, and that comprises means (6) for recording the locations of threshold value exceedances for the wafers (W) to be inspected; and a second optical inspection device (4) for examination, only at those locations at which a threshold value exceedance is identified, of the wafers (W) to be inspected, which also comprises a classification device. The scattered-light measuring instrument (3) and the second optical inspection device (4) are arranged in one production line (P) as sequentially located stations. The first optical inspection device (2), on the other hand, is arranged outside the production line (P). A corresponding method is also described.

21 Claims, 1 Drawing Sheet

ARRANGEMENT AND METHOD FOR INSPECTING UNPATTERNED WAFERS

CROSS REFERENCE TO RELATED APPLICATIONS

Figure 1:
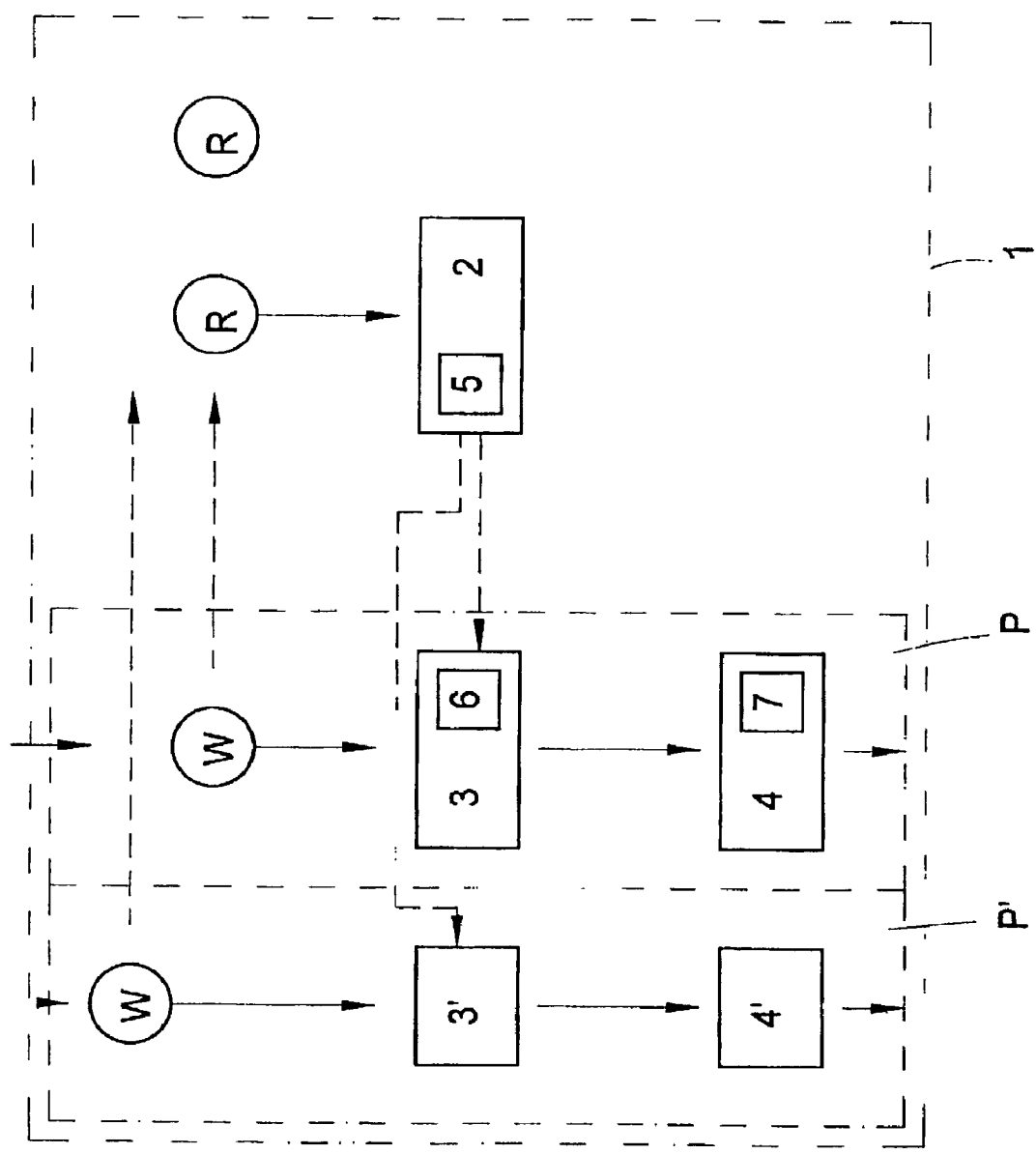

This application claims priority of the German patent application 101 41 051.4 which is incorporated by reference herein.

FIELD OF THE INVENTION

The invention refers to an arrangement for inspecting preferably unpatterned wafers, and furthermore to a method for inspecting wafers. The invention is suitable in particular for the recognition of epitaxial defects.

BACKGROUND OF THE INVENTION

During the manufacture of wafers, defects can occur on their surface which later substantially impair the function of the components to be manufactured from the wafers, or make them unusable. Defects in the crystal structure of the wafers, in particular in an epitaxial layer (called "epitaxial defects"), have proven to be especially troublesome in this context.

Epitaxial defects occur, for example, in the silicon layer as a result of disruptions in crystal growth. The usual cause is excessively rapid crystal growth during manufacture of the epitaxial layer, which is deposited, for example, in a CVD process using trichlorosilane at temperatures of approximately 1150° C. Contaminants can also cause epitaxial defects.

Because of their effects on the components to be manufactured, it is of interest to prevent occurrence of the aforesaid defects or, since that is usually not possible with sufficient reliability, to know the exact number and location of the defects present on a wafer. As a rule, a maximum of approximately three defects with sizes in the range up to a few tens of µm are tolerated on a wafer having a diameter of 8 inches.

A number of methods and apparatuses for the detection of epitaxial defects are disclosed in a presentation entitled "Discrimination of defects on epitaxial silicon wafers" published in Electrochemical Society Proceedings, Vol. 97/22, pp. 438 ff.

For example, it is known to examine unpatterned wafers by means of an optical inspection device, for example a microscope. For that purpose, essentially the entire surface of a wafer to be inspected, with the exception of a very narrow edge region that is not used for the production of components, is scanned.

The image data thereby obtained are examined for the presence of defects using image data processing methods known per se. This procedure is very time-consuming, however, given the very small physical extent of the possible defects. Several hours are therefore required for analysis of the image data of a single 8-inch wafer. Thus, although unpatterned wafers can in principle be examined with sufficient accuracy for the presence of defects, this procedure is nevertheless unsuitable for checking wafers in industrial production because of the immense time requirement.

So-called scattered-light measuring instruments, with which the local scattered-light intensity on a wafer is determined, are therefore used in this context. Less time is required for this. Practical investigations, however, for example those described in the publication cited above, indicate that not all epitaxial defects can be discovered with such instruments and methods. In the investigation cited, in the best case 96% of all epitaxial defects were detected. It must also be considered in this context that with the scattered-light method it is not possible to distinguish between epitaxial defects, non-epitaxial defects, and artifacts (i.e. false defects).

This means that ultimately what is determined with a scattered-light examination is not the presence of a defect but merely an exceedance beyond a threshold value, with no possibility of concluding what that threshold value exceedance can be attributed to. Classification of the defects is thus not possible. Investigations have furthermore shown that the scattered-light method usually indicates considerably more defects than are actually present, but that on the other hand defects are also overlooked.

In the publication cited above, it was therefore suggested that a wafer first be examined with a scattered-light measuring instrument and that the locations of a threshold value exceedance be recorded so they can later be examined more closely in an optical inspection device. In the latter, a classification of the defects can simultaneously also be performed. By limiting the reinspection to the locations of a threshold value exceedance, it is in principle possible to integrate a microscopic examination, which would take too long for an examination of the entire wafer, into an inspection method that is suitable for the industrial production of wafers. The time for a reinspection at a location with a threshold value exceedance is only on the order of approximately one second. The accuracy and efficiency of the entire method thus depend on the number of threshold value exceedances identified in the scattered-light measuring instrument.

SUMMARY OF THE INVENTION

Proceeding therefrom, it is the object of the invention to create an arrangement and a method with which, to the greatest extent possible, all defects on preferably unpatterned wafers can be quickly discovered and qualified as such.

The present invention proposes an arrangement for inspecting wafers that comprises: a first optical inspection device for examining reference wafers, which operates using image data processing methods and thereby recognizes defects on the reference wafers; a scattered-light measuring instrument that is calibrated with the reference wafers by defining at least one threshold value for the recognition of defects on wafers to be inspected, and that comprises means for recording the locations of threshold value exceedances for the wafers to be inspected; and a second optical inspection device for examining the wafers to be inspected only at the locations at which a threshold value exceedance is identified, which also comprises a classification device which is configured so that the threshold value exceedances can be classified using image data processing methods. The scattered-light measuring instrument and the optical inspection device are preferably arranged in a production line as sequentially located stations, whereas the first optical inspection device is arranged outside the production line.

The arrangement according to the present invention makes possible a method for inspecting unpatterned wafers having the following steps: an offline examination of reference wafers, defects on the reference wafers being recognized using image data processing methods; a calibration of a scattered-light measuring instrument with the reference wafers, by defining at least one threshold value for the recognition of defects; an inline examination, using the scattered-light measuring instrument, of wafers to be inspected, and recording of the locations of threshold value exceedances; and an inline examination, at the locations at which a threshold value exceedance is identified, of the wafers to be inspected, image data processing methods being used in order to classify the methods.

Both the arrangement and the method are suitable in particular for recognizing epitaxial defects on unpatterned wafers.

With calibration of the scattered-light measuring instrument on the basis of known defects using the reference wafers, the invention makes possible an optimization of the results obtained in the scattered-light measurement. Using the reference wafers, the threshold values for generating a defect signal at the scattered-light measuring instrument are optimized in such a way that on the one hand all defects that cause a threshold value exceedance are detected, and on the other hand the number of artifacts is minimized. As a result, the number of locations to be examined in the subsequent second optical inspection device is in turn minimized, with the overall result of enabling rapid defect determination and reliable defect qualification.

The classification device allows the known defects to be associated with various causes. In particular, it is possible reliably to determine defects in the crystal structure, or epitaxial defects, and to output their location as well as, optionally, their type on a list associated with the particular wafer, which serves as a quality certificate for the wafer.

Because only the scattered-light measuring instrument and the second inspection device are arranged in the production line, a high wafer throughput is achieved. Each wafer passes through these two examination steps. In that way it can be rapidly evaluated and given an individual certificate.

The first optical inspection device, on the other hand, is used "offline," i.e. outside the actual production line. It can therefore also be used, for example, in conjunction with several different production lines.

For particularly high accuracy in the localization of crystal defects or epitaxial defects, the threshold value or values is or are set on the scattered-light measuring instrument in such a way that every defect present on a reference wafer results in a threshold value exceedance. The result of this is very high reliability, so that every crystal defect or epitaxial defect actually present on a wafer is in fact found.

In an advantageous embodiment of the arrangement according to the present invention, the scattered-light measuring instrument and the optical inspection device are arranged physically separately from one another. This enables parallel examination of multiple wafers, so that a particularly high throughput of wafers for inspection can be achieved. The examination with the scattered-light measuring instrument and/or the examination of the locations with an identified threshold value exceedance are preferably performed automatically. This again contributes to a high throughput rate.

In this context, it is additionally advantageous if the inline examination using the scattered-light measuring instrument and the inline examination of the locations having a threshold value exceedance in the second optical inspection device are synchronized with the working cycle of the production line. This makes possible a continuous production process with integrated quality monitoring and certification step.

The locations of the threshold value exceedances for each wafer to be inspected are preferably recorded automatically on a list. That list is then transferred to the subsequent second optical inspection device. The term "list" is to be understood broadly here. It encompasses, in particular, all types of data records that represent an association between an identified threshold value exceedance and the relevant location on the wafer.

On the basis of this list, the pertinent locations are traveled to in the second optical inspection device and examined more closely. For that purpose, its classification device is preferably configured so that the locations entered on the list have associated with them the particular class that is identified, which is recorded in association with the respective location. The classes can, for example, be based on defect type in order distinguish different crystal defects or epitaxial defects from one another. Additional classes can furthermore be provided for further defect types and artifacts.

Common methods based, for example, on fuzzy logic or neural networks are used for classification in the context of image data processing. The input variables used for image data processing are predominantly local brightness values. When these values are correlated with one another, information about the particular defect type can be derived, for example, from differences in the brightness and color, physical extent, and shape of the defect identified. Appropriate feature combinations can then be used to define a class.

The association between the identified classes and the particular location of a threshold value exceedance yields detailed information about the defects present on a wafer. With this more-accurate knowledge, it is also conceivable that wafers formerly considered rejects can continue to be at least partially used for the manufacture of electronic components.

In order to improve the calibration of the scattered-light measuring instrument, it is advantageous if the types of defects on the reference wafers are taken into consideration. Preferably, therefore, a classification of defects is performed already during the offline examination of the reference wafers. The classification is preferably performed according to the same criteria or with the same evaluation algorithms in the context of the offline examination and the inline examination.

DETAILED DESCRIPTION OF THE INVENTION

The invention will be explained in more detail below with reference to an exemplary embodiment depicted in the drawings, in which FIG. 1 is a schematic view of an arrangement for inspecting unpatterned wafers.

What is depicted is an arrangement 1 with which crystal defects in an epitaxial silicon layer, i.e. so-called epitaxial defects, on a silicon substrate can be detected. FIG. 1 shows in this context, by way of example, two mutually independent production lines P and P' of a continuous or quasi-continuous, e.g. batch-operated, wafer production process.

All that is shown in the exemplary embodiment, however, is the region of interest for the inspection of wafers W, with the devices present therein for inline examination.

In its minimum configuration, arrangement 1 comprises a first optical inspection device 2 arranged offline (i.e. outside production line P or P'), a scattered-light measuring instrument 3 arranged inline (i.e. within production line P and/or P'), and a second optical inspection device 4 arranged within production line P and/or P' and after said instrument in the transport direction of the wafers.

Whereas scattered-light measuring instrument 3 and inspection device 4 are each traversed by wafers W that are to be inspected, first optical inspection device 2 is used for the examination of reference wafers R. These reference wafers R can in principle be any wafers W for inspection that have been taken out of the production process.

Reference wafers R selected in this fashion are completely examined for defects in first optical inspection device 2. Because of the large number of locations to be examined, this is generally performed automatically with the use of image data processing methods. For example, the evaluation or classification can be performed on the basis of predefined criteria. This does not, however, rule out "manual" evaluation of individual defects.

In the exemplary embodiment depicted, first optical inspection device 2 is a microscope having an automatic image acquisition system. What is used for image acquisition is, for example, a video camera with which, in coaction with the microscope and suitable feed devices, the entire region of interest on reference wafers R can be sequentially scanned at a resolution close to that of the expected defects, i.e. on the order of one im to several tens of μm.

The image data obtained during the scanning operation are processed in real time, i.e. at the fastest possible system speed. This means that each image of the wafer, representing only a very small partial view in each case, is analyzed for defects in a classification device 5 at the working rate of the video camera. For that purpose, different types of defects, defined by way of individual features but preferably by combinations of features, are defined in classification device 5.

The defect types can, for example, be permanently preprogrammed, taking into account brightness and color data as well as the size and shape of the defects as criteria. A class definition based on fuzzy logic or neural networks is also possible. Neural networks, in particular, offer a very good opportunity to train classification device 5 using known defects.

Despite the real-time image processing, complete examination of a reference wafer R with a diameter of 8 inches requires several hours in this instance for the classification of defects having the dimensions cited above, so that inspection device 2 is used exclusively for the analysis of reference wafers R. A very precise defect description over the entire surface on a wafer that is of interest for further processing is then available, however, for reference wafers R.

Reference wafers R are used to calibrate scattered-light measuring instrument 3. Instruments of this kind are commonly known, so no further explanation is necessary here for one skilled in the art. They are based on the principle of acquisition and analysis of brightness intensities in the light coming from a wafer W that is to be inspected. A variety of parameters can be set depending on the type of instrument. It is thereby possible to detect deviations from a value that is expected for a defect-free region.

In the present exemplary embodiment, for each threshold value exceedance the location currently being examined on wafer W is recorded, suitable means 6 for the purpose being provided. The threshold values are set using reference wafers R, particular attention being paid to examination of those defects known on reference wafers. Using reference wafers R, the threshold values are set so that to the greatest extent possible, only the critical errors result in a threshold value exceedance. On the other hand, however, this ensures that every defect present on a reference wafer R results in a threshold value exceedance. Since the usability of the wafer is greatly influenced especially by crystal structure defects or epitaxial defects, in this exemplary embodiment the threshold value settings are oriented principally toward recognition of those kinds of defects. It is also possible in principle, however, by way of a specific threshold value setting in conjunction with reference wafer R, to optimize scattered-light measuring instrument 3 for other defect types.

Since, in the present case, a threshold value exceedance is desired for every crystal structure defect or epitaxial defect, threshold value exceedances based on other defects or on artifacts are initially also tolerated in the context of the inline inspection in scattered-light measuring instrument 3. These are then examined more closely in the downstream second optical inspection device 4.

Second optical inspection device 4, which is arranged physically separately from scattered-light measuring instrument 3, serves for inline examination, exclusively at those locations at which a threshold value exceedance was identified using scattered-light measuring instrument 3, of wafers W that are to be inspected. The corresponding location data are transmitted to second optical inspection device 4 in the form of a list.

On the basis of that list, for example a data record, the aforementioned locations on the wafer can be specifically traveled to and examined more closely. For that purpose, second optical inspection device 4 is here once again embodied as a microscope that coacts with an automatic image acquisition device, for example a further video camera. In addition, second optical inspection device 4 comprises a classification device 7 in the form of an electronic computation and storage device, so that the acquired image data can be analyzed with regard to defect type using image data processing methods, and the threshold value exceedances that have been identified can thereby be classified.

The procedure corresponds to that for the classification of defects on reference wafers R in classification device 5 of first optical inspection device 2. Emphasis here, however, is placed not on real-time processing but on maximum certainty in classification of the threshold value exceedances recorded on the list of scattered-light measuring instruments 3. The respectively identified classes are associated with the locations indicated on the list, and recorded in association with the respective location. The final defect list resulting therefrom then serves to certify the inspected wafer W, indicating the number and position of the crystal structure defects or epitaxial defects present on wafer W. Moreover, the final defect list can additionally indicate the defect type, i.e., for example, a distinction can be made between different types of crystal structure defects or epitaxial defects.

The arrangement described above makes possible fully automatic generation of defect lists for each individual wafer in a continuous production line or manufacturing process. Several production lines P and P' can also be operated alongside one another. This is depicted in FIG. 1 by way of example. In this case more than one scattered-light measuring instrument 3 and second optical inspection device 4 are present, as indicated in FIG. 1 by the reference characters 3' and 4'. First optical inspection device 2, on the other hand, is in principle required only once. The entire inspection operation on a production line P or P' proceeds automatically, and is synchronized with the working cycle of the production line.

The arrangement described above, like the associated method, allows all defects on unpatterned wafers to be quickly discovered and qualified as such.

PARTS LISTS

1 Arrangement
2 Optical inspection device
3, 3' Scattered-light measuring instrument
4, 4' Optical inspection device
5 Classification device
6 Means
7 Classification device
P, P' Production line
R Reference wafer
W Wafer

What is claimed is:

1. An arrangement for inspecting wafers and recognizing epitaxial defects on unpatterned wafers, comprising:
   a first optical inspection device, arranged outside a production line, for examining unpatterned reference wafers, which operates using image data processing methods and serves to recognize defects on the reference wafers, wherein the reference wafers are wafers out of a production process;
   a scattered-light measuring instrument, arranged in the production line, that is calibrated on the basis of the reference wafers by defining at least one threshold value serving for the recognition of defects on unpatterned wafers to be inspected, and that comprises a recording device for recording the locations at which the threshold values are exceeded on a wafer to be inspected; and
   a second optical inspection device, arranged in the production line, which is provided for examination, only at the locations at which a threshold value exceedance was identified, of the unpatterned wafers to be inspected, and which comprises a classification device that classifies the threshold value exceedances using image data processing methods.

2. The arrangement as defined in claim 1, wherein the scattered-light measuring instrument and the second optical inspection device are arranged in the production line as sequentially located stations.

3. The arrangement for inspection of unpatterned wafers as defined in claim 1, wherein the scattered-light measuring instrument and the second optical inspection device are arranged physically separately from one another.

4. The arrangement as defined in claim 1, wherein the threshold value or values is or are selected in such a way that every defect present on a reference wafer (R) results in a threshold value exceedance.

5. The arrangement as defined in claim 1, wherein the inline examination in the scattered-light measuring instrument, and the inline examination in the second optical inspection device of the locations having a threshold value exceedance, are synchronized with the working cycle of the production line.

6. The arrangement as defined in claim 1, wherein the locations of the threshold value exceedances for each wafer to be inspected are automatically recorded on a list, and the respective list is transferred to the subsequent second optical inspection device.

7. The arrangement as defined in claim 6, wherein the inline examination in the second optical inspection device is accomplished on the basis of the locations entered on the list; and the classification device of the second optical inspection device is configured so that the locations entered on the list have associated with them the particular class that is identified, which is recorded in association with the respective location.

8. The arrangement as defined in claim 1, wherein the arrangement is arranged to inspect wafers in multiple production lines.

9. The arrangement as defined in claim 1, wherein the first optical inspection device is adapted to examine unpatterned reference wafers with defects inherent to the production process.

10. A method for inspecting wafers and recognizing epitaxial defects on unpatterned wafers, having the following steps:
    examining unpatterned reference wafers offline using a first optical inspection device, defects on the reference wafers being recognized using image data processing methods, wherein the first optical inspection device is arranged outside a production line;
    calibrating a scattered-light measuring instrument based on the examination of the reference wafers, by defining at least one threshold value for the recognition of defects;
    examining the unpatterned wafers to be inspected inline using the scattered-light measuring instrument, arranged in the production line, and recording the locations of threshold value exceedances; and
    examining the unpatterned wafers to be inspected inline, using image data processing methods and a second optical inspection device, arranged in the production line, at the locations at which a threshold value exceedance is identified, the defects being classified.

11. The method as defined in claim 10, wherein the inline examination using the scattered-light measuring instrument and the inline examination of the locations with a threshold value exceedance are performed in stations physically separated from one another.

12. The method as defined in claim 10, wherein the examination using the scattered-light measuring instrument is performed automatically.

13. The method as defined in claim 10, wherein the examination of the locations with a threshold value exceedance is performed automatically.

14. The method as defined in claim 10, wherein the inline examination using the scattered-light measuring instrument and the inline examination of the locations with a threshold value exceedance are performed synchronously with the working cycle of a continuous production line.

15. The method as defined in claim 10, wherein in the context of the inline examination using the scattered-light measuring instrument, a list is automatically recorded which contains the locations of the threshold value exceedances, and the subsequent inline examination is performed on the basis of the locations entered on the list.

16. The method as defined in claim 15, wherein the locations entered on the list have associated with them the particular class that is identified, which is recorded in association with the respective location.

17. The method as defined in claim 10, wherein in the context of the offline examination of the reference wafers, a classification of the defects is performed.

18. The method as defined in claim 10, wherein the classification is accomplished according to the same criteria during the inline examination and during the classification in the context of the offline examination.

19. The method as defined in claim 10, wherein the reference wafers are wafers out of a production process.

20. The method as defined in claim 8, wherein wafers are inspected in multiple production lines.

21. The method as defined in claim 10, wherein the defects examined by the first optical inspection device are inherent to a production process.

* * * * *